United States Patent [19]

Neti

[11] 4,272,248
[45] Jun. 9, 1981

[54] NITRIC OXIDE INTERFERENCE FREE SULFUR DIOXIDE FLUORESCENCE ANALYZER

[75] Inventor: Radhakrishna M. Neti, Brea, Calif.

[73] Assignee: Beckman Instruments, Inc., Fullerton, Calif.

[21] Appl. No.: 107,109

[22] Filed: Dec. 26, 1979

[51] Int. Cl.³ ............................................. G01N 21/64
[52] U.S. Cl. .............................. 23/232 R; 23/232 E; 250/576; 422/91
[58] Field of Search .......................... 23/232 R, 232 E; 422/88, 91, 52; 73/23; 250/373, 461, 576

[56] References Cited

U.S. PATENT DOCUMENTS

| 3,652,227 | 3/1972 | Harman et al. | 23/232 R |
| 3,677,708 | 7/1972 | Harman et al. | 23/232 R |
| 4,077,774 | 3/1978 | Neti et al. | 23/232 R |

Primary Examiner—Ronald Serwin
Attorney, Agent, or Firm—Robert J. Steinmeyer; Paul R. Harder; Edward C. Jason

[57] ABSTRACT

In a sulfur dioxide fluorescence analyzer, a method and apparatus for eliminating the fluorescence effects of nitric oxide is disclosed wherein a sample gas is mixed with a diluent which substantially quenches nitric oxide fluorescence.

14 Claims, 3 Drawing Figures

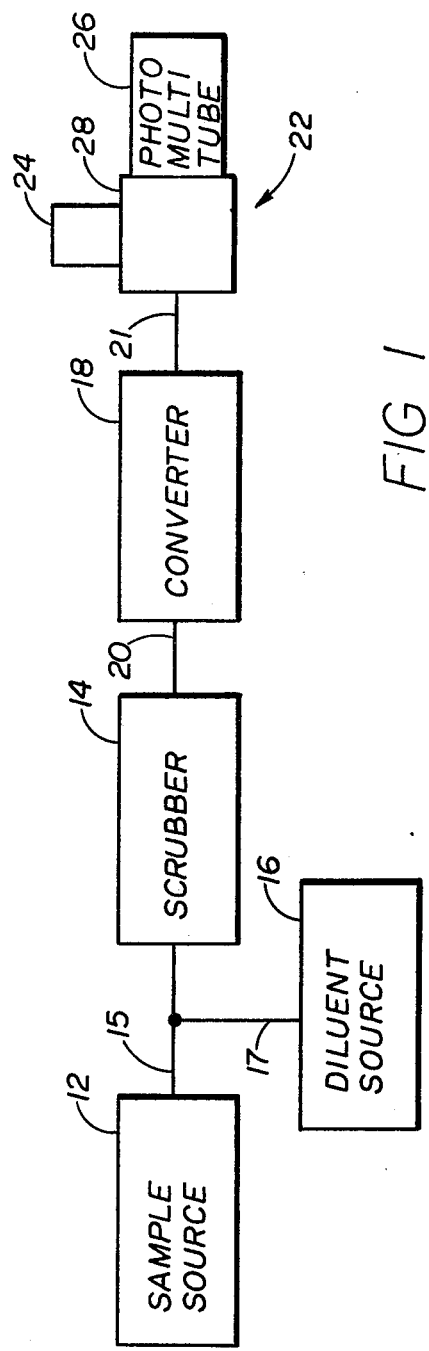
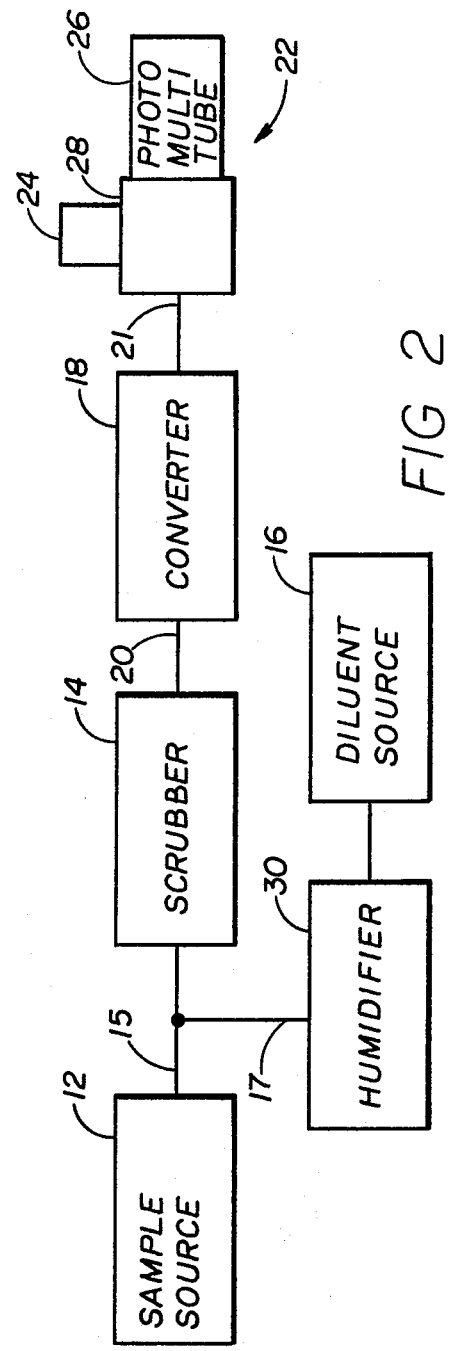

NITRIC OXIDE INTERFERENCE FREE SULFUR DIOXIDE FLUORESCENCE ANALYZER

BACKGROUND OF THE INVENTION

The present invention pertains to fluorescence analyzers and more particularly fluorescence analyzers used in determining sulfur dioxide content in a sample stream of gas.

In sulfur dioxide analyzers, the sample input stream containing sulfur dioxide to be analyzed is presented to a reaction chamber in which it is illuminated by an ultraviolet light source. Sulfur dioxide molecules present absorb the incident radiation, increase in energy content momentarily and then release the absorbed energy at a longer wavelength than the incident radiation (fluorescence). The fluorescence radiation is detected at right angles to the incident radiation by a photomultipler tube and electrically amplified to be displayed as the signal proportional to the concentration of sulfur dioxide present in the input gas sample. Further details of fluorescent methodology may be found disclosed in U.S. Pat. No. 3,795,812 to Hideo Okabi.

Other compounds exist in sample streams containing sulfur dioxide which also fluoresce in a similar fashion to the fluorescence exhibited by sulfur dioxide. Polynuclear aeromatic hydrocarbons (such as naphthalene, anthracene, penanthracene, etc.) were generally considered the principal class of compounds which exhibit this behavior, for which a method and apparatus to remove their interferent effects is disclosed in copending U.S. Patent application Ser. No. 12,174 to John N. Harman III, assigned to the same assignee as this application. However, the interferent effects of nitric oxide are now realized to produce interferent fluorescence and are not removed by existing prior art methods or apparatus. Nitric oxide fluoresces in a manner similar and at a similar wavelength to sulfur dioxide. While most applications of sulfur dioxide fluorescent analyzers have only negligible effects from nitric oxide, applications of sulfur dioxide fluorescent analyzers, such as measuring sulfur dioxide in automobile exhaust emissions, are plagued with nitric dioxide fluorescence to the extent that the indication of sulfur dioxide may be double its actual concentration.

From known prior art, the only solution to this problem is to perform a fluorescent analysis to determine the sulfur dioxide content of the sample and to perform a nitric dioxide analysis by a method other than fluorescence analysis. The nitric oxide content may then be subtracted from the indicated sulfur dioxide content to achieve a true sulfur dioxide content.

SUMMARY OF THE INVENTION

The present invention pertains to the removal of interferent fluorescence effects in fluorescent analysis of sulfur dioxide. A new method and apparatus is disclosed wherein a sample stream containing sulfur dioxide is intermixed with oxygen or in a second embodiment wherein it is intermixed with a humidified stream of gas. Nitric oxide and other interferents fluoresce in approximately the same wavelength as sulfur dioxide. Both water vapor and oxygen serve to quench fluorescence properties exhibited by interferents such as nitric oxide while exhibiting no effect on the fluorescence of sulfur dioxide.

BRIEF DESCRIPTION OF THE DRAWINGS

FIG. 1 is a block flow diagram of a sulfur dioxide analysis system constructed in accordance with this invention.

FIG. 2 is a block flow diagram of a sulfur dioxide analysis system constructed in accordance with a second embodiment of the present invention.

DESCRIPTION OF THE PREFERRED EMBODIMENT

Figure 3:
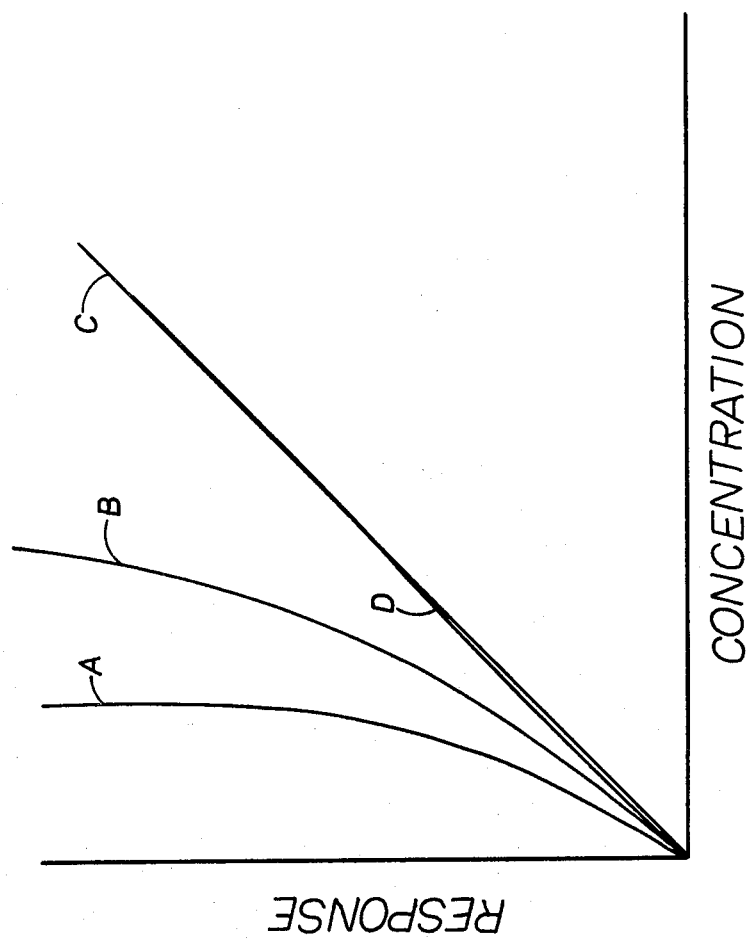
FIG. 3 is a graphical representation of the output of sulfur dioxide analysis systems of FIGS. 1 and 2.

FIG. 1 illustrates a sample source 12 connected to a scrubber 14 through a conduit 15. Conduit 15 is connected to a diluent source 16 through a conduit 17. Scrubber 14 is connected to a converter 18 through a conduit 20. Converter 18 is connected through a conduit 21 to a fluorescent analyzer 22 having an ultraviolet source 24 and a photomultiplier tube 26 connected to a housing 28.

In actual operation, source 12 supplies a source of sample gas for which the concentration of sulfur dioxide is to be measured through conduit 15 to scrubber 14. Sample source 12 may be of any type which provides a sample stream of gas for analysis. In some cases it may be the exhaust of an automobile, while in others it may be a sample extracting pipette in a smoke stack. Diluent source 16 provides a diluent gas through conduit 17 to intermix with the sample gas stream in conduit 15 prior to its input to scrubber 14. The diluent gas is preferably oxygen to quench the fluorescent activity of nitric oxide which fluoresces at a wavelength which gives the apparency of sulfur dioxide fluorescence. Scrubber 14 is typically a housing containing a mixture of mercuric chloride with Teflon or a copper powder deposited on Teflon to remove hydrogen sulfide and various mercaptans. Mercaptans such as $C_2H_5SH$ and other sulfur containing species such as $H_2S$ will produce sulfur dioxide when combined with oxygen under heat which will increase the sulfur dioxide reading. Once hydrogen sulfide and mercaptans are removed by scrubber 14, the sample gas stream is then passed to converter 18 through conduit 20. Converter 18 is typically a housing containing amorphous graphite heated to approximately 400° C. However, as disclosed in copending U.S. application Ser. No. 12,174 a mixture of vanadium pentoxide may be used with superior results for removing polynuclear aeromatic hydrocarbons. The sample gas stream mixed with diluent gas, after having the mercaptans and polynuclear aeromatic hydrocarbons removed is transmitted to fluorescent analyzer 22 through conduit 21. Fluorescent analyzer 22 comprises an ultraviolet source 24 which produces incident ultraviolet rays on the gas sample to be measured in housing 28. Sulfur dioxide molecules absorb the incident radiation, increase in energy content momentarily and then release the absorbed energy at a longer wavelength than the incident radiation. The fluorescent radiation is detected by photomultiplier tube 26, electrically amplified and displayed as a signal proportional to the concentration of sulfur dioxide present in the gas sample. Also within housing 28, nitric oxide molecules absorb the incident radiation, and also increase in energy momentarily and then release the absorbed energy at a wavelength approximately the same as sulfur dioxide. Without diluent source 16, fluorescent radiation of sulfur dioxide and nitric oxide will be detected by photomultiplier tube 26 and is displayed as though the fluorescence were due to an increased amount of sulfur dioxide instead of sulfur dioxide and nitric oxide. In supplying oxygen in the sample stream to be measured, the fluorescence due to excitation of nitric oxide molecules will be quenched by the presence of oxygen.

The centerpoint wavelength of the band of energy released by nitric oxide to fluorescence is slightly different than the centerpoint of the band of energy released by sulfur dioxide. However, the centerpoints of the two bands are extremely close together and there is sufficient overlapping of the two bands to prevent the effective use of narrow band filters to remove the fluorescence effects of nitric oxide. Oxygen molecules, on the other hand, are highly selective in the energy which they quench.

A Beckman Model 953 Sulfur Dioxide Fluorescent Analyzer was used in combination to establish reduction to practice for the present invention. This analyzer employs a deuterium lamp from which the exciting radiation of 2115 Angstroms is isolated with a narrow band interference filter. The sample is illuminated in a 316 stainless steel cell. The emitted fluorescence of sulfur dioxide is detected at right angles to the incident light with a blue sensitive photomultiplier tube and associated electronics. The sample is conditioned by selectively scrubbing the polynuclear aeromatics and other sulfur compounds by passing the sample through the appropriate scrubbers as detailed in the foregoing description. It has been found that this analyzer performs satisfactorily in analyzing ambient air containing sulfur dioxide and nitric oxide, as long as the ambient air is reasonably humid and the nitric oxide levels are relatively low. However, continued sampling of nitric oxide in dry nitrogen blends with this analyzer shows an almost equivalent response to nitric oxide as sulfur dioxide. This strong interference of nitric oxide was reduced to different levels by blending the sample of nitric oxide with ambient air of varying relative humidity levels. The reduction increased as the relative humidity increased, indicating that water vapor exhibits nitric oxide fluorescence quenching properties.

In an additional typical experiment a sample blend was made by dynamically blending 500 cubic centimeters per minute of 50 parts per million sulfur dioxide in nitrogen with 250 cubic centimeters per minute of oxygen. This decreased the signal of sulfur dioxide from 50 parts per million, full scale, to approximately 34 parts per million due to dilution of the sample. When this mixture was further blended with 250 cubic centimeters per minute of 10,000 parts per million of nitric oxide in dry nitrogen the response decreased due to dilution with no appreciable increase due to nitric oxide fluorescence. Without the oxygen, the response of the fluorescent analyzer would have increased substantially due to nitric oxide fluorescence. When the nitric oxide/nitrogen diluent was replaced with the same amount of oxygen, the response of the analyzer decreased slightly (approximately 2.2 ppm) indicating that oxygen substantially but not totally eliminates nitric oxide response in a fluorescence analysis. A response of 2.2 ppm out of 10,000 ppm means that oxygen quenching of nitric oxide fluorescence is about 99.97% effective. Without the oxygen, the fluorescence analyzer indicates an additional 2500 ppm of sulfur dioxide due to the presence of nitric oxide. With the oxygen present, as indicated previously, the error was reduced to approximately 2.2 ppm. Further experimentation indicated that ratio of oxygen to nitric oxide of approximately forty to one yields the maximum nitric oxide fluorescence quenching. The interference of 2.2 ppm may be further eliminated by interposing an additional filter between the photomultiplier and the sample cell.

In order to determine whether the decreased response to nitric oxide is due to the oxidation of nitric oxide to nitrogen dioxide, or by actual quenching of nitric oxide fluorescence by oxygen, the dynamically blended nitric oxide plus sulfur dioxide plus oxygen was mixed and analyzed on a Beckman Model 951 NO-$NO_x$ Analyzer. A determination was made that only approximately 6.4% of the nitric oxide was converted to nitrogen dioxide indicating that the quantitative diminution of nitric oxide response was due to quenching by oxygen. While oxygen acts as a strong quencher of nitric oxide fluorescence, it is also possible to quench nitric oxide fluorescence by the embodiment illustrated in FIG. 2.

Referring now to FIG. 2, the fluorescent analyzer system of FIG. 1 is illustrated with the addition of humidifier 30 inserted in conduit 17 between diluent source 16 and conduit 15. In the second embodiment diluent source 16 supplies a gas, such as ambient air, through humidifier 30 to be mixed with the sample stream of gas from source 12. As indicated previously, water vapor acts to quench fluorescent activity by nitric oxide when excited by ultraviolet source 24. Thus, a diluent gas which has been humidified will act to quench nitric oxide fluorescence. As with oxygen, a ratio of water vapor to nitric oxide of approximately forty to one is necessary for sufficient quenching. As such, water vapor or humidity in a gas not having nitric oxide fluorescence quenching properties can only be used to quench fluorescence of low nitric oxide levels. However, nitric oxide fluorescence quenching capability may be increased if ambient air, having an oxygen concentration of approximately 20%, is supplied as the diluent gas. For this example, humidifier 30 acts to humidify the ambient air from diluent source 16 to a level wherein the quenching properties of the oxygen in ambient air are augmented to satisfactorily quench the fluorescence of nitric oxide at higher nitric oxide ppm levels than either water vapor or oxygen alone.

It has been suggested to humidify the sample stream of gas prior to fluorescence analysis; however, several problems are encountered. First, humidification of a sample containing sulfur dioxide, to be effective, must be done by slowly bubbling the sample through water, a process which increases the total sample analysis time. And second, sulfur dioxide will form sulfurous acid in this process which slowly forms sulfuric acid. Thus, intermixing the sample of gas with a humidified diluent stream of gas is preferred.

Referring now to FIG. 3, a graphical representation having indicated response on its ordinates and actual concentration of sulfur dioxide on its abscissas is illustrated. Curve A illustrates the indicated response of a dry sample gas having nitric oxide and sulfur dioxide contained therein. As illustrated, the actual concentration of sulfur dioxide is significantly less than the indicated response. Curve B illustrates the indicated response for a sample gas stream containing nitric oxide and sulfur dioxide when mixed with ambient air. Although curve B gives a closer indication of the actual concentration of sulfur dioxide as opposed to the indicated response, it still contains significant deviation from curve C which represents the ideal correlation between indicated response and actual concentration. Curve D represents the indicated response of the same sample of curves A and B wherein the sample is mixed with pure oxygen or humidified air. As can be seen, curve D tracks curve C almost perfectly, with slight deviations occurring due to less than total quenching.

It is important to note that while water vapor exhibits nitric oxide fluorescence quenching properties, water vapor alone is limited to low levels of nitric oxide. As indicated previously, a ratio of water vapor to nitric oxide of approximately forty to one is necessary to satisfactorily quench nitric oxide fluorescence. A carrier or diluent gas at room temperature, approximately 22° C., and 100% relative humidity, the diluent gas is approximately 2.6% $H_2O$, or 26,000 ppm $H_2O$. This amount of water vapor reduces to 13,000 ppm when mixed with an equal volume of a dry sample. Thus, after mixing, the concentration of nitric oxide can be no greater than 325 ppm, which is 650 ppm prior to mixing. If ambient air is the humidified diluent, the 20% oxygen in ambient air, 200,000 ppm, raises the fluorescence quenching level to 5650 (200,000/40+650) ppm nitric oxide prior to mixing. As can be realized, increasing the level of oxygen in the diluent stream will increase the quenchable levels of nitric oxide in a sample stream of gas. Additionally, if a greater proportional amount of the diluent gas is supplied, higher levels of nitric oxide fluorescence may be quenched. However, increasing the proportion of the diluent stream can reduce the ppm levels of the component of interest, sulfur dioxide, to a degree that increases the percent error of the measurement.

It is also to be noted that while both of the foregoing embodiments illustrate the mixing point of the sample stream and the diluent stream prior to scrubber 14, it is to be understood by one skilled in the art that the sample stream and diluent stream may be intermixed at any point prior to fluorescent analyzer 22, such as at conduit 21.

The foregoing description of the preferred embodiment is shown by way of example only and is not to be considered as limiting, since many variations may be made by those skilled in the art without departing from the scope or spirit of the invention which is to be construed only in light of the following claims.

What is claimed is:

1. A method for removing the fluorescence effect of nitric oxide in a fluorescence analyzer that measures sulfur dioxide comprising the steps of:
   providing a sample stream of gas;
   providing a diluent stream of gas containing at least one component having nitric oxide quenching properties;
   intermixing said sample stream and said diluent stream to form a mixture; and
   supplying said mixture to the fluorescence analyzer.

2. The method of claim 1 wherein said step of providing a diluent stream of gas comprises providing a diluent stream of gas having a high oxygen concentration.

3. The method of claim 1 wherein said step of providing a diluent gas stream comprises the step of providing humidified ambient air as said diluent stream.

4. A method for removing the fluorescence effects of nitric oxide in a fluorescent analyzer system for measuring the sulfur dioxide content in a sample stream of gas comprising:
   providing a sample stream of gas;
   providing a diluent stream of gas containing a component exhibiting quenching properties for nitric oxide fluorescence;
   intermixing said sample stream and said diluent stream forming a sample mixture; and
   supplying said mixture to the fluorescent analyzer.

5. The method of claims 2, 3 or 4 also including the step of:
   receiving said mixture in a scrubber wherein hydrogen sulfide and mercaptans are removed.

6. The method of claim 5 including the additional step of receiving said mixture in a converter wherein polynuclear aromatic hydrocarbons are removed.

7. In combination:
   conduit means for receiving a sample stream of gas containing nitric oxide as an interferent;
   diluent means for providing a diluent stream of gas containing a component exhibiting quenching properties for quenching nitric oxide fluorescence;
   mixing means for intermixing said sample stream and said diluent stream to form a sample mixture; and
   analyzer means for receiving said sample mixture and analyzing said sample mixture for sulfur dioxide by fluorescence.

8. The combination of claim 7 wherein said diluent stream comprises a stream of gas containing oxygen.

9. The combination of claim 8 wherein the concentration of said oxygen is such that the oxygen to nitric oxide ratio of said sample mixture is at least approximately forty to one.

10. The combination of claim 7 wherein said diluent stream comprises humidified ambient air.

11. The combination of claim 10 wherein said humidified ambient air is such that the water vapor plus oxygen to nitric oxide ratio of said sample mixture is at least approximately forty to one.

12. The combination of claims 8 or 10 also including means for removing hydrogen sulfide and mercaptans from said sample stream.

13. The combination according to claims 8 or 10 also including means for removing hydrogen sulfide and mercaptans from said sample mixture.

14. The combination according to claims 8 or 10 also including means for removing polynuclear aromatic hydrocarbons.

* * * * *